United States Patent
Hoffmann et al.

(10) Patent No.: US 7,582,686 B2
(45) Date of Patent: Sep. 1, 2009

(54) HYDROLYSIS-STABLE MONOMERS WITH ACID GROUPS

(75) Inventors: Marcus Hoffmann, Usingen (DE); Albert Erdrich, Bad Nauheim (DE)

(73) Assignee: Heraeus Kulzer GmbH, Hanau (DE)

( * ) Notice: Subject to any disclaimer, the term of this patent is extended or adjusted under 35 U.S.C. 154(b) by 494 days.

(21) Appl. No.: 11/328,742

(22) Filed: Jan. 10, 2006

(65) Prior Publication Data

US 2006/0160920 A1    Jul. 20, 2006

(30) Foreign Application Priority Data

Jan. 17, 2005    (DE)    ........................ 10 2005 002 330

(51) Int. Cl.
- *A61K 6/083*    (2006.01)
- *C08F 10/14*    (2006.01)
- *C08L 33/14*    (2006.01)

(52) U.S. Cl. .................... 523/116; 524/560; 526/292.1; 433/228.1

(58) Field of Classification Search ................. 523/116; 524/560; 526/292.1
See application file for complete search history.

(56) References Cited

U.S. PATENT DOCUMENTS

| | | | |
|---|---|---|---|
| 4,755,620 | A | 7/1988 | Iwamoto et al. |
| 6,172,131 | B1 | 1/2001 | Moszner et al. |
| 6,710,149 | B2 | 3/2004 | Moszner et al. |
| 6,812,266 | B2 | 11/2004 | Klee et al. |
| 2003/0055124 | A1 | 3/2003 | Klee et al. |
| 2003/0187094 | A1 | 10/2003 | Klee et al. |

FOREIGN PATENT DOCUMENTS

| | | |
|---|---|---|
| DE | 10101523 | 8/2002 |
| DE | 10206451 | 8/2003 |
| DE | 10234326 | 2/2004 |
| DE | 10242106 | 4/2004 |
| EP | 1421927 | 5/2004 |
| EP | 1479364 | 11/2004 |
| EP | 1548021 | 6/2005 |
| WO | WO 03035013 | 5/2003 |
| WO | WO 03070198 | 8/2003 |

*Primary Examiner*—Tae H Yoon
(74) *Attorney, Agent, or Firm*—Norris McLaughlin & Marcus PA

(57) ABSTRACT

Compounds of the formula I $$R^1-O-CO-C(=CHR)-Y-O-Q(AH)_n \qquad (I)$$

where

A stands for a —$CO_2$— or —$SO_3$— group which together with $H^+$ yields AH,

Q represents $C_{1-12}$alkylene, $C_{4-12}$alkylene interrupted by —O—, >N—, or —S—, or, in given cases, $C_{6-15}$arylene substituted with $C_{1-4}$alkyl, $C_{1-4}$alkoxy or halogen, where in the case of arylene the aryl groups can carry additional acid groups A, Y stands for $C_{1-12}$alkylene or $C_{4-12}$alkylene interrupted by —O—, >N—, or —S—, R represents methyl or H, $R^1$ is $C_{1-6}$alkyl, and n assumes the values 1, 2, or 3
are particularly suitable for the production of self-etching dental adhesives.

5 Claims, No Drawings

HYDROLYSIS-STABLE MONOMERS WITH ACID GROUPS

The invention relates to hydrolysis-stable monomers with acid groups, their production, and their use.

BACKGROUND OF THE INVENTION

For a few years self-etching adhesives have been known in the field of dentistry. They combine an etching and bonding step so that the surface is prepared for the polymer or composite filling. They are as a rule two-component materials which must be either mixed directly before their application or applied sequentially. One of the first single-component, single-flask adhesives in which no mixing or sequential application of two components is required came onto the market with iBOND™ Gluma Inside (Heraeus Kulzer). It can be considered as a disadvantage that iBOND™ Gluma Inside must be stored cold (4-10° C.) since there is the possibility that due to a hydrolysis of the components during storage at higher temperatures a short-term polymerization will occur in the packaging.

Various hydrolysis-stable monomers for dental materials have already been proposed, among them sulfonic acid derivatives with (WO03070198A1, US20030187094A1) and without siloxane groups (US20030055124A1) as well as acrylester phosphonic acids and their esters (U.S. Pat. No. 6,710,149B2, DE10206451A1, U.S. Pat. No. 6,172,131B1, U.S. Pat. No. 6,812,266B2) WO03035013A1), or carboxylic acid derivatives with PO-containing groups (DE10242106A1).

For example, in the product Adhese (Ivoclar Vivadent) a hydrolysis-stable phosphonic acid ether acrylate is added as an acidic component.

In the use of self-etching dental adhesives the steps of conditioning and subsequent application of the adhesive (bonding) are combined into one step. A previous, separate etching of the hard substances of the tooth (enamel, dentin) with phosphoric acid is omitted. In the case of the dentin the acid-containing adhesive systems dissolve the smear layer and expose the underlying dentin or make the smear layer penetrable for the adhesive. Simultaneously to this, the infiltration of the monomers into the hard substances of the tooth takes place. In the case of the enamel an etching pattern similar to that of phosphoric acid etching is produced by the acid-containing adhesive system. Subsequently, the solvent necessary for the etching process and for infiltration is removed with an air cushion and the adhesive hardened by irradiation.

Self-conditioning adhesives contain as active component acidic monomers capable of polymerization. As a rule these monomers are (meth)acrylic acid esters of organic or inorganic acids. As examples of acidic monomers let phosphoric acid esters, such as HEMA phosphate, or esters of trimellitic acid or trimellitic acid anhydride be named.

From organic chemistry it is known that esters in acidic, aqueous solution are not hydrolysis-stable. Accordingly, hydrolytic cleavage can occur during storage of said acidic monomers in aqueous solutions within a few weeks to months. Thus it can be shown that in the hydrolysis of HEMA phosphate the compounds methacrylic acid, HEMA, and phosphoric acid are released. The rate of hydrolysis is, among other things, dependent on the pH value temperature and runs clearly more slowly in cold storage.

The objective is presented of providing hydrolysis-stable monomers which are suitable for the production of self-conditioning adhesives.

SUMMARY OF THE INVENTION

It has been found that ether compounds of organic acids or their anhydrides represent an additional path to hydrolysis-stable acidic monomers with outstanding etching and bonding properties, alone or in combination with other acidic monomers.

DETAILED DESCRIPTION

The invention relates to compounds of the formula I

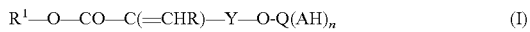

$$R^1-O-CO-C(=CHR)-Y-O-Q(AH)_n \qquad (I)$$

where

A stands for a $-CO_2$ or $-SO_3$ group which together with $H^+$ yields AH,

Q represents $C_{1-12}$alkylene, $C_{4-12}$alkylene interrupted by $-O-$, $>N-$, or $-S-$, or, in given cases, $C_{6-15}$arylene substituted with $C_{1-4}$alkyl, $C_{1-4}$alkoxy or halogen, where in the case of arylene the aryl groups can carry additional acid groups A, Y stands for $C_{1-12}$alkylene or $C_{4-12}$alkylene interrupted by $-O-$, $>N-$, or $-S-$, R represents methyl or H, $R^1$ is $C_{1-6}$alkyl, and n assumes the values 1, 2, or 3.

$R^1$ as $C_{1-6}$alkyl means, for example, methyl, ethyl, n-propyl, n-butyl, n-pentyl, n-hexyl, or their isomeric forms.

Y or Q as $C_{1-12}$alkylene stand, for example, for methylene, ethylene, propylene, tetramethylene, pentamethylene, 2,2-dimethyltrimethylene, hexamethylene, heptamethylene, octamethylene, decamethylene, or dodecamethylene.

By $C_{4-12}$alkylene groups interrupted by $-O-$, $>N-$, or $-S-$ are meant, for example, $-CH_2-O-CH_2CH_2-O-CH_2-$, $-CH_2-(O-CH_2CH_2)_2-O-CH_2-$, $-CH_2-(O-CH_2CH_2)_3-O-CH_2-$, $-CH_2-(O-CH_2CH_2)_4-O-CH_2-$, and in particular $-CH_2CH_2-O-CH_2CH_2-O-CH_2CH_2-$, $-CH_2CH_2-Nme-CH_2CH_2-$ or $-CH_2CH_2-S-CH_2CH_2-$, where Me is methyl.

$C_{6-15}$arylene can be, for example, o-phenylene, m-phenylene, p-phenylene, 1,4-napthylene, and 4,4'-diphenylene.

$C_{6-15}$arylene substituted with $C_{1-4}$alkyl, $C_{1-4}$alkoxy or halogen are, for example, the above-mentioned o-phenylene, m-phenylene, p-phenylene, 1,4-napthylene, and 4,4'-diphenylene which are substituted on the ring with $-CH_3$, $-C_2H_5-$, $OCH_3$, or Cl.

The compounds of the formula I can in particular be used as a component of adhesives, cements, composites, and formed bodies as well as preferably dental materials. In so doing, it is possible that they are present in at least partially polymerized form.

With the use of the hydrolysis-stable, acidic, polymerizable monomers of the formula I in an adhesive formulation, stability during storage is improved. In combination with additional hydrolysis-stable and polymerizable molecules cold storage is no longer necessary to ensure long-term stability.

The compounds of the formula I are suitable in particular for dental adhesives for fastening direct fillers such as composites, compomers, and ormocers.

Accordingly, the invention also relates to compositions containing

A at least one compound of the formula I,

B at least one additional polymerizable monomer,

C one or more initiators as well as, in given cases, materials from the groups of D fillers, pigments, stabilizers, UV absorbers, dyes, or lubricants.

Such adhesives can be used advantageously in connection with an additional layer which neutralizes or covers the acidic components and a fastening element for the fastening of indirect, laboratory-ready fillers of, for example, ceramics or composite.

The compounds of the formula I are suitable as an additive in fissure sealers or esthetic lacquers.

Polymerizable monomers, initiators, fillers, pigments, and stabilizers are known to those skilled in the dental art.

As traditional, radically polymerizable monomers difunctional cross-linking monomers are suitable in particular. For the production of adhesives or dental materials cross-linking bifunctional or multifunctional acrylates or methacrylates, such as, for example, bishphenol-A-di(meth)acrylate, the addition product of methacrylic acid and bishphenol-A-diglycidylether denoted as bis-GMA, the addition product of hydroxyethylmethacrylate and 2,2,4-trimethylhexamethylene diisocyanate denoted as UDMA, diethylene glycol di(meth)acrylate, triethylene glycol di(meth)acrylate, or tetraethylene glycol di(meth)acrylate, decanediol di(meth)acrylate, trimethylolpropane tri(meth)acrylate, and pentaerythrite tetra(meth)acrylate are suitable. The compounds butanediol (meth)acrylate, 1,10-decanediol di(meth)acrylate, and 1,12-dodecanediol di(meth)acrylate accessible by esterification of (meth)acrylic acid with the corresponding diols are also suitable.

Moreover, the compositions according to the invention are filled with organic or inorganic particles or fibers for the improvement of their mechanical properties. Preferred inorganic particulate fillers are amorphous, spherical materials on the basis of mixed oxides of $SiO_2$, $ZrO_2$ and/or $TiO_2$, microfine fillers, such as pyrogenic silicic acid or precipitated silicic acid, as well as macrofillers, microfillers, or nanofillers, such as quartz, glass ceramics, or glass powder with an average particle size of 0.001 to 5 μm. Finally, X-ray-opaque fillers, such as ytterbium trifluoride, glass fibers, polyamide fibers, or carbon fibers can also be used.

The compositions according to the invention can, if need be, contain additional components, above all solvents, such as water, ethyl acetate, acetone, ethanol, or mixtures of these, as well as stabilizers, UV absorbers, dyes, pigments, or lubricants.

The compounds of the formula I are suited in particular as a component of dental adhesives and means for etching and bonding of dentin or dental enamel but also of additional dental materials such as fastening cements, restoration composites, underfilling materials, dental lacquers, and fissure sealants. Such materials distinguish themselves by very good adhesion to various substrates such as the hard substances of the tooth and metallic substrates. Accordingly, the invention also relates to those materials containing compounds of the formula I as well as the use of compounds of the formula I for their production.

The hydrolysis stability of compounds of the formula I also imparts a very good hydrolysis stability to the materials according to the invention. That applies to non-polymeric as well as the polymerizable material. High hydrolysis stability is naturally of particular importance for those materials which are permanently exposed to aqueous materials as is precisely the case for dental materials which are provided for a long retention in the oral cavity.

To carry out the polymerization the known radical initiators (cf. Encyclopedia of Polymer Science and Engineering, Vol. 13, Wiley-Interscience Publisher, New York, 1988, 754 ff.) can be used. Azocompounds such as azobis(isobutylnitrile) (AIBN) or azobis-(4-cyanovaleric acid) or peroxides such as dibenzoylperoxide, dilaurylperoxide, tert.-butylperoctoate, tert.-butylperbenzoate, or di-(tert.-butyl)-peroxide are suitable.

As initiators for the hot-hardening benzpinacol and 2,2'-dialkylbenzpinacol are also suitable.

Furthermore, photoinitiators (cf. J. P. Fouassier, J. F. Rabek (Editor), Radiation Curing in Polymer Science and Technology, Vol. II, Elsevier Applied Science, London and New York, 1993) for the polymerization with UV light or light at visible wavelengths such as benzoin ether, dialkylbenzyl ketals, dialkoxyacetophenones, acylphosphine oxides, alpha-diketones, such as 9,10-phenanthrenquinone, diacetyl, furil, anisil, 4,4'-dichlorobenzil, and 4,4'-dialoxybenzil, and camphor quinone, can also be used.

The production of the compounds of the formula I is done according to processes known per se, for example, by reacting a compound of the formula II

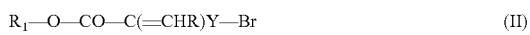
$$R_1—O—CO—C(=CHR)Y—Br \qquad (II)$$

with a compound of the formula IIII

$$HO-Q(AL)_n \qquad (III),$$

where L represents a protective group which replaces the protons.

Preferably the reaction is carried out in an aprotic solvent, preferably in dimethylformamide (DMF). It is advantageously started at room temperature. Exothermy can make cooling necessary.

The following example explains a form of embodiment of the invention without the invention being restricted thereto (percentages relate to weight in so far as nothing is noted to the contrary):

EXAMPLE 1

4-(2-ethoxycarbonyl-allyloxy)-phthalic Acid

Intermediate Intermediate Product A1: "5-hydroxy-1,2-dicarboxylic Acid"

Starting materials: 100 ml of 4-sulfophthalic acid tech 50% in water (d=1.292), 131.4 g of NaOH pellets The 4-sulfophthalic acid solution is carefully treated in a steel beaker with the first 30 g of NaOH pellets. In so doing, the mixture heats up to the boiling point. Two added boiling stones prevent longer boiling delays. The beaker is immersed in the oil bath preheated to 210° C. and adds while stirring with a spatula the remaining NaOH pellets in portions. During their introduction some foaming continues to be observed which can be kept under control by stirring and intermittent short lowering of the bath. After complete addition within approximately 30 minutes the bath temperature is lowered to 200° C. and the suspension is allowed to react accompanied by intermittent movements of the spatula for 2 more hours.

The suspension is then poured out onto a steel plate and during hardening made rough with the spatula in order to obtain a larger surface. It is dissolved with a total of 1.5 liters of water and poured into a beaker glass. It is made acidic with 340 ml of HCl under ice cooling from outside. Meanwhile the temperature is intermittently allowed to increase to 50° C. After the acidification ca. two liters of an almost colorless clear solution are obtained.

The solution is extracted once with 500 ml of ethyl acetate and twice 300 ml of ethyl acetate.

The organic phases are washed twice with 150 ml of diluted saline water and once with 100 ml of concentrated saline water. After drying over MgSO$_4$ one filters, concentrates by evaporation, and dries on the Rotavapor. 42.2 g of colorless crystals (86%) result as raw product.

The raw product together with the raw product of an additional batch (40.6 g) with 400 ml of ethyl acetate is heated for 30 minutes. After cooling to room temperature it is let stand overnight. The suspension is cooled in the ice bath, filtered, and washed with ice-cold ethyl acetate.

After filtering it is dried in the dry cabinet at the house vacuum at 50° C.

Recrystallization from ethyl acetate yields 68.26 g of colorless crystals, flash point 202-203° C., yield 71.5% relative to 0.524 moles.

HPLC and NRM yield an isomer-free product.

Intermediate Product A: 5-hydroxyphthalic Acid Anhydride

The flask with the product from step 1 is immersed in an oil bath preheated to ca. 200° C. After several minutes the previously colorless crystals take on a brownish color and then with slight foaming pass over into a pale brown melt. After 30 minutes the flask is lifted out of the bath. Crystallization immediately occurs again.

The raw product was 0.39 g. According to NMR, HPLC, and LC-MS as SO1081.015 raw.

Flash point; as of 162° C. sintering, 164-169° C. melting.

The product should be recrystallized together with a later batch.

Intermediate Intermediate Product B1 2-hydroxymethyl Acrylic Acid Ethyl Ester 16.2 ml of CH$_2$O solution (37%) in water are combined with 65.2 ml of acrylic acid ethyl ester, 1800 ml of dioxan, and 22.4 g of DABCO and stirred at room temperature. After 14 hours the progress of the reaction is checked via HPLC. The solvent was first distilled off on the Rotavapor at ca. 40 ° C. bath temperature and <70 mbar pressure. Along with this the excess acrylic ester also distills off. The remaining clear aqueous solution is extracted in the separating funnel three times with methyltert.butylether. The extracts are washed twice with saline water, dried over Mg sulfate, filtered, and concentrated by evaporation.

Intermediate Product B: 2-bromomethyl Acrylic Acid Ethyl Ester 10 g of 2-hydroxymethyl acrylic acid ethyl ester are presented in ether, cooled to 15° C., and 3.2 ml (9.26 g) of PBr3 are added dropwise within 5 minutes. One removes the cooling and stirs for 2 hours at room temperature.

From the colorless solution a very small amount of a white precipitate has separated. One cools again to −15° C. and adds 100 ml of water dropwise. Initially this was exothermic with the development of gas but after that ca. 10 ml are added dropwise and the rest can be run in rapidly. The phases are separated and the aqueous phase extracted with diethylether (3×50 ml). The combined organic phases are washed twice with water and once with saline water, dried with M9SO4 [sic], filtered, and concentrated by evaporation. The result is 13.67 g of clear, light yellow liquid.

4-(2-ethoxycarbonyl-allyloxy)-phthalic Acid

The intermediate products A (11.55 g) and B (13.67 g) are presented in 100 ml of DMF with stirring and 4.65 g of potash are added at room temperature. One notices immediately a yellow coloration of the suspension and a slight development of gas. The reaction is weakly exothermic. As a precaution one places a cold water bath under the flask as cooling. It is left stirring at room temperature for 2 hours.

After preparation one obtains 20.52 g of dry, colorless, crystalline residue.

The raw product is dissolved with 80 ml of ethyl acetate while boiling and the yellowish solution filtered.

Subsequently, enough ethyl acetate is drawn off on the Rotavapor at ca. 200 mbar that a final weight of the solution of ca. 61 g results. This corresponds to a remaining ethyl acetate portion of ca. 47 g. On seeding the product begins to crystallize out in colorless, very fine crystal needles. It is treated with 20 ml of ether and cooled in the ice bath. After filtering it is washed with an ice-cold ethyl acetate/ether mixture and dried in the vacuum drying cabinet at 40° C.

Yield 10.52 g (50.8%) of colorless crystals.

Flash point: −147° C.

The mother liquor is boiled down and the residue, which has once again become crystalline, is digested with ether. After 3 hours it is filtered at room temperature and washed with ether. After drying in a vacuum the result is 2.54 g (12.2%) of colorless crystals as a second fraction.

EXAMPLE 2A-D

Test of Efficacy as Acidic Monomer in an Adhesive Formulation

The following preparations are produced by intensive mixing of the components.

| Example 2 | A | B | C | D |
|---|---|---|---|---|
| Urethane dimethacrylate | 10 | 15 | 20 | 25 |
| 4-(2-ethoxycarbonyl-allyloxy)-phthalic acid | 20 | 15 | 10 | 5 |
| Acetone | 40 | 40 | 40 | 40 |
| Water | 30 | 30 | 30 | 30 |
| Camphor quinone | 0.2 | 0.2 | 0.2 | 0.2 |
| 2-n-butoxyethyl-4-(dimethylamino)benzoate | 0.3 | 0.3 | 0.3 | 0.3 |

Efficacy as acidic monomer in an adhesive formulation is tested by determination of the shear bonding strength on dentin and enamel. Human teeth are used which have been stored in 0.5% chloramine-T solution for at most three months after extraction. Before use in the bonding test the teeth are carefully cleaned under flowing water. On the day before use in the bonding test the teeth are individually imbedded, lying on an approximal side, in cylindrical rubber forms with Technovite 4001. The teeth are ground by wet-grinding with SiC papers of the grains 80, 240, and finally 600 until a sufficiently large dentin or enamel surface for the bonding of a plastic cylinder with a 3.5 mm diameter is exposed. After rinsing with desalinated water the teeth are dried in an air stream. On the tooth surface the preparations from examples 2A-D are applied with a brush in three layers, dried in a compressed air stream, and irradiated with the light device Translux® Energy (Heraeus Kulzer) for 20 seconds. The sample thus pre-treated is then clamped fast by means of a clamping device under a two-part cylindrical Teflon form (3.5 mm diameter, 1 mm height). Thereafter the plastic filler Charisma® (Heraeus Kulzer) is filled into the Teflon form, covered with an oxygen-impermeable PE foil, and irradiated with the light device Translux® Energy (Heraeus Kulzer) for 20 seconds. Immediately thereafter the Teflon form is taken off and the cylindrical sample stored for 24 hours in 37° C. water until the introduction of the shear load. For that, the cylindrical sample is loaded in a universal test machine with the aid of a pressure piston parallel to and tight on the ground tooth surface with a speed of 1 mm/min until separation of the plastic cylinder from the tooth. The shear bonding strength is the quotient of the breaking load and the bonding area and is determined for each of 8 samples, where their average value is given in the table.

Results:

| Preparation | Shear Bonding Strength on Dentin [MPa] | Shear Bonding Strength on Enamel [MPa] |
| --- | --- | --- |
| 2A | 17.0 | 6.4 |
| 2B | 17.1 | 7.0 |
| 2C | 24.6 | 9.8 |
| 2D | 12.9 | 6.2 |

The measurement of the shear adhesion bonding on dentin and enamel confirms that the compound of the formula I, 4-(2-ethoxycarbonyl-allyloxy)-phthalic acid, is effective as an acidic monomer in adhesives.

The invention claimed is:

1. Compounds of the formula I

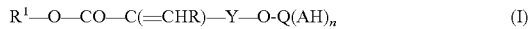

where

A represents a —$CO_2$— group which together with $H^+$ yields AH,

Q represents $C_{6-15}$arylene substituted with $C_{1-4}$alkyl, $C_{1-4}$alkoxy or halogen, where in the case of arylene the aryl groups carry at least one additional —$CO_2$— group A, Y represents $C_{1-12}$alkylene or $C_{4-12}$alkylene interrupted by —O—, >N—, or —S—, R represents methyl or H, $R^1$ is $C_{1-6}$alkyl, and n assumes the values 2 or 3.

2. Process for the production of compounds of the formula I, wherein a compound of the formula II

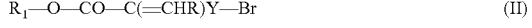

is reacted with a compound of the formula III

where L represents a protective group which replaces the protons.

3. Compositions containing

A at least one compound of the formula I according to claim 1,

B at least one additional polymerizable monomer,

C one or more initiators as well as, optionally,

D fillers and/or pigments and/or stabilizers.

4. Dental materials containing at least one compound of the formula I according to claim 1.

5. Dental materials according to claim 4 in the form of fastening cements, restoration composites, underfilling materials, dental lacquers, and fissure sealants or means for etching and bonding of dentin or dental enamel.

* * * * *